United States Patent [19]

Kaeding

[11] 4,393,262

[45] * Jul. 12, 1983

[54] PRODUCTION OF ISOPROPYLBENZENE

[75] Inventor: Warren W. Kaeding, Westfield, N.J.

[73] Assignee: Mobil Oil Corporation, New York, N.Y.

[*] Notice: The portion of the term of this patent subsequent to Sep. 22, 1998, has been disclaimed.

[21] Appl. No.: 969,626

[22] Filed: Dec. 14, 1978

[51] Int. Cl.$^3$ .................. C07C 63/34; B01J 29/06
[52] U.S. Cl. ................ 585/467; 252/455 Z
[58] Field of Search ............ 260/671 P, 672 T, 671; 423/328; 252/455 Z; 585/467

[56] References Cited

U.S. PATENT DOCUMENTS

| | | | |
|---|---|---|---|
| 2,881,227 | 4/1959 | Kiezer | 260/671 |
| 2,904,607 | 9/1959 | Mattox et al. | 585/467 |
| 3,251,897 | 5/1966 | Wise | 585/467 |
| 3,385,906 | 5/1968 | Kaufman | 260/671 |
| 3,702,886 | 11/1972 | Argauer et al. | 423/328 |
| 3,751,504 | 8/1973 | Keown et al. | 585/467 |
| 3,751,506 | 8/1973 | Burress | 585/467 |
| 3,755,483 | 8/1973 | Burress | 260/671 R |
| 3,776,971 | 12/1973 | Carr et al. | 260/671 P |
| 3,778,415 | 12/1973 | Ko | 260/672 T |
| 3,832,449 | 8/1974 | Rosinski et al. | 252/455 Z |
| 3,843,739 | 10/1974 | Harper et al. | 260/672 T |
| 4,016,245 | 4/1977 | Plank et al. | 423/328 |
| 4,046,859 | 4/1977 | Plank et al. | 423/328 |
| 4,049,737 | 9/1977 | Dwyer et al. | 260/671 P |
| 4,070,407 | 1/1978 | Haag et al. | 260/671 R |
| 4,076,842 | 2/1978 | Plank et al. | 252/455 Z |
| 4,291,185 | 9/1981 | Kaeding | 423/328 |

OTHER PUBLICATIONS

*Chemical Abstracts* vol. 89 #6023u, Kolesnikov et al. 1978 "Alkylation of Benzene by Propylene and N-butylenes under Pressure in Liq. Phase".

*Chemical Abstracts* vol. 71 #100994m; Allakhverdieva et al. 1969, "Kinetics of the Alkylation of Benzene by Propylene on Y-type Zeolites."

*Chemical Abstracts* vol. 89 #132224y, Mobil Oil, 1977 "Alkylation or Transalkylation of Aromatic Hydrocarbons".

*Primary Examiner*—Delbert E. Gantz
*Assistant Examiner*—Raymond K. Covington
*Attorney, Agent, or Firm*—Charles A. Huggett; Ronald J. Cier; George W. Allen

[57] ABSTRACT

A process is disclosed whereby benzene is brought into contact with propylene, in the presence of a specified type of crystalline zeolite catalyst, to produce isopropylbenzene. The preferred zeolite catalysts are those having a silica to alumina ratio of at least about 12 and a constraint index, as herein defined, within the approximate range of 1–12. The process may be carried out in the liquid or the vapor phase at temperatures of from about 100° C. to about 300° C. and pressures ranging from $10^5$ N/m$^2$ to $6 \times 10^6$ N/m$^2$.

10 Claims, No Drawings

4,393,262

PRODUCTION OF ISOPROPYLBENZENE

BACKGROUND OF THE INVENTION

1. Field of the Invention

This invention relates to a process for the selective production of isopropylbenzene by catalytic propylation of benzene in the presence of a particular crystalline zeolite catalyst.

2. Description of the Prior Art

Alkylation of aromatic hydrocarbons utilizing crystalline zeolite catalysts has heretofore been described. U.S. Pat. No. 2,904,607 to Mattox refers to alkylation of aromatic hydrocarbons with an olefin in the presence of a crystalline metallic aluminosilicate having uniform pore openings of about 6 to 15 Angstrom unit. U.S. Pat. No. 3,251,897 to Wise describes alkylation of aromatic hydrocarbons in the presence of X- or Y-type crystalline zeolites, specifically such type zeolites wherein the cation is rare earth and/or hydrogen. U.S. Pat. No. 3,751,504 to Keown et al. and U.S. Pat. No. 3,751,506 to Burress describe vapor phase alkylation of aromatic hydrocarbons with olefins in the presence of a specified type of zeolite catalyst.

U.S. Pat. No. 3,755,483 to Burress discloses vapor phase alkylation of aromatic hydrocarbons in the presence of ZSM-12 zeolite catalyst. The reaction is carried out at temperatures between the critical temperature of the aromatic compound and 482° C. (900° F.). The critical temperature and pressure of benzene are 288.9° C. (552° F.) and 48.6 atm. ($4.9 \times 10^6$ N/m$^2$).

Harper et al. have described the catalytic alkylation of benzene with propylene over a crystalline zeolite (Petrochemical Preprints, American Chemical Society, Vol. 22, No. 3, p. 1084, 1977). Extensive kinetic and catalyst aging studies were conducted with a rare earth-exchanged Y-type zeolite (REY) catalyst.

While the above-noted prior art is considered of interest in connection with the subject matter of the present invention, the propylation reaction described herein carried out at a temperature of between about 100° C. and about the critical temperature in the presence of the particular type of catalyst disclosed to selectively yield isopropylbenzene has not, insofar as is known, been heretofore described.

SUMMARY OF THE INVENTION

In accordance with the present invention, there is disclosed herein a novel process for selectively producing isopropylbenzene by catalytic alkylation of benzene with propylene in the presence of a particular kind of crystalline siliceous zeolite, said zeolite having a silica to alumina ratio of at least about 12 and a constraint index within the approximate range of 1 to 12. The process may be carried out in both heterogeneous gas/-solid and liquid/solid phases at temperatures ranging from about 100° C. to about the critical temperature, and preferably within the appoximate range of 150° C. to 250° C. The catalytic agent particularly preferred comprises the crystalline zeolite designated ZSM-12.

Description of Specific Embodiments

The crystalline zeolites utilized herein are members of a novel class of zeolites that exhibits unusual properties. Although these zeolites have unusually low alumina contents, i.e. high silica to alumina ratios, they are very active when the silica to alumina ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by controlled burning at higher than usual temperatures to restore activity. These zeolites, used as catalysts, generally have low coke-forming activity and, therefore, are conducive to long times on stream between regenerations by burning with oxygen-containing gas such as air.

An important characteristic of the crystal structure of this class of zeolites is that it provides constrained access to and egress from the intracrystalline free space by virtue of having an effective pore size intermediate between the small pore Linde A and the large pore Linde X, i.e. the pore windows of the structure have about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra. Briefly, the preferred type zeolites useful in this invention possess, in combination: a silica to alumina mole ratio of at least about 12 and a structure providing constrained access to the intracrystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than hexane is excluded and the zeolite is not of the desired type. Windows of 10-membered rings are preferred, although in the some instances excessive puckering of the rings or pore blockage may render these zeolites ineffective.

Although it is thought that twelve-membered rings usually do not offer sufficient constraint to produce advantageous conversions, it is noted that the puckered 12-ring structure of TMA offretite shows constrained access. Other 12-ring structures may exist which may be operative and it is not the intention to judge the usefulness herein of a particular zeolite merely from theoretical structural considerations.

Rather than attempt to judge from crystal structure whether or not a zeolite possesses the necessary constrained access to molecules larger than normal paraffins, a simple determination of the "Constraint Index" as herein defined may be made by passing continuously a mixture of an equal weight of hexane and 3-methylpentane over a small sample, approximately one gram or less, of the zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature adjusted between 290° C. and 510° C. to give an overall conversion between 10% and 60%. The mixture of hydrocarbons is passed at 1 liquid hourly space velocity (i.e. 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical zeolites are:

| ZEOLITE | C.I. |
| --- | --- |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Beta | 0.6 |
| ZSM-4 | 0.5 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different Constraint Indices. Constraint Index seems to vary somewhat with severity of operation (conversion) and the presence or absence of binders. Therefore, it will be appreciated that it may be possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the novel class of highly siliceous zeolites are those zeolites which, when tested under two or more sets of conditions within the above specified ranges of temperature and conversion, produce a value of the Constraint Index slightly less than 1, e.g. 0.9, or somewhat greater than 12, e.g. 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove to have a Constraint Index of 1 to 12 is intended to be included in the instant catalyst definition regardless that the same identical zeolite tested under other defined conditions may give a Constraint Index value outside of 1 to 12.

The class of zeolites defined herein is exemplified by ZSM-5, ZSM-11, ZSM-12, ZSM-23, ZSM-35, ZSM-38, and other similar materials. U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-23 is more particularly described in U.S. Pat. No. 4,076,842, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. No. 4,046,859, the entire content of which is incorporated herein by reference.

The specific zeolites described, when prepared in the presence of organic cations, are substantially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be treated include ferrierite, brewsterite, stilbite, dachiardite, epistilbite, heulandite, and clinoptilolite.

Of the zeolite materials described by the above parameters, it has been found that ZSM-12 is especially useful in the hereindisclosed process. Said ZSM-12 is, therefore, particularly preferred in the practice of the present invention.

In a preferred aspect of this invention, the zeolites hereof are selected as those having a crystal framework density, in the dry hydrogen form, of not less than about 1.6 grams per cubic centimeter. It has been found that zeolites which satisfy all three of these criteria are most desired for several reasons. When hydrocarbon products or by-products are catalytically formed, for example, such zeolites tend to maximize the production of gasoline boiling range hydrocarbon products. Therefore, the preferred zeolites of this invention are those having a Constraint Index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g. on Page 19 of the article of Zeolite Structure by W. M. Meier. This paper, the entire contents of which are incorporated herein by reference, is included in "Proceedings of the Conference on Molecular Sieves, London, April 1967," published by the Society of Chemical Industry, London 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space. It is possible that the unusual sustained activity of this class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | | 1.8 |
| ZSM-23 | | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired alkylation process, it may be desirable to incorporate the above described crystalline zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix on an anhydrous basis may vary widely with the zeolite content ranging from between about 1 to about 99 percent by weight and more usually in the range of about 5 to about 80 percent by weight of the dry composite.

Propylation of benzene in the presence of the above-described catalyst is effected by contact of the benzene with propylene at a temperature between about 100° C. and about the critical temperature, and preferably between about 150° C. and 250° C. The reaction generally takes place at atmospheric pressure, but the pressure may be within the approximate range of $10^5$ N/m$^2$ to $6 \times 10^6$ N/m$^2$ (1 atm to 60 atm). The molar ratio of benzene to propylene is preferably within the approximate range of 12:1 to 1:1. The reaction may be suitably accomplished utilizing a feed weight hourly space velocity (WHSV) of between about 0.5 and about 100, preferably between about 5 and about 40.

The process of this invention may be conducted with the organic reactants in either the gaseous or the liquid phase or both. It may be carried out as a batch-type, semi-continuous or continuous operation utilizing a fixed, fluidized or moving bed catalyst system.

The following examples will serve to illustrate the process of this invention without being limiting thereon:

EXAMPLE 1

A sample of HZSM-12 crystalline zeolite catalyst was intimately mixed with 35 wt. % alumina binder, then pressed into wafers, crushed and screened to a uniform particle size of 14–20 mesh. Benzene and propylene, in a mole ratio of 9.5/1, were passed over the catalyst at 200° C. and WHSV of 31.0 (benzene) and 1.8 (propylene). Holding the temperature and feed rate constant, the pressure was varied from 0 to 125 psig. The products of the reaction were collected, weighed and analyzed using standard laboratory techniques. The results are summarized in TABLE I.

TABLE I

| CONDITIONS OF REACTION | | | | | | |
|---|---|---|---|---|---|---|
| Temp. °C. | 200 | 200 | 200 | 200 | 200 | 200 |
| Press. psig | 0 | 25 | 50 | 75 | 100 | 125 |
| WHSV Benzene | 31.0 | 31.0 | 31.0 | 31.0 | 31.0 | 31.0 |
| WHSV Propylene | 1.8 | 1.8 | 1.8 | 1.8 | 1.8 | 1.8 |
| Mole Ratio Benzene/Propylene | 9.5 | 9.5 | 9.5 | 9.5 | 9.5 | 9.5 |
| CONVERSION, Wt % | | | | | | |
| Benzene | 8.4 | 9.5 | 9.6 | 10.3 | 10.3 | 10.3 |
| Propylene | 92.6 | 97.0 | 97.5 | 94.8 | 95.1 | 94.8 |
| SELECTIVITY TO PRODUCTS, Wt % | | | | | | |
| Isopropylbenzene | 83.8 | 86.8 | 88.6 | 88.5 | 89.8 | 90.4 |
| Diisopropylbenzene | 13.4 | 11.7 | 10.4 | 9.7 | 8.6 | 8.0 |
| n-Propylbenzene | 0 | 0 | 0 | 0 | 0 | 0 |
| Other | 2.8 | 1.5 | 1.0 | 1.8 | 1.6 | 1.6 |
| Total | 100.0 | 100.0 | 100.0 | 100.0 | 100.0 | 100.0 |

As will be seen, benzene conversion increased gradually with pressure, going from 8.4% to 10.3% (the theoretical maximum was 10.5% based on the limiting amount of propylene in the feed and assuming isopropylbenzene is the only product). Excellent performance was observed with selectivity to isopropylbenzene approaching 90%, a most unexpected result for such mild conditions of reaction. Diisopropylbenzene accounted for all but about 1–1.5% of the remaining product. Under these conditions, the organic products and starting materials were in the vapor phase.

EXAMPLE 2

In a manner similar to that described in Example 1, and using a similar catalyst, the reaction was studied at pressures of from 100–350 psig. The temperature was again at 200° C., but the mole ratio and WHSV for benzene to propylene were 6.6/1 and 30/2.4, respectively. The reaction is summarized in TABLE II.

TABLE II

| CONDITIONS OF REACTION | | | | | | |
|---|---|---|---|---|---|---|
| Temp. °C. | 200 | 200 | 200 | 200 | 200 | 200 |
| Press. psig | 100 | 150 | 200 | 250 | 300 | 350 |
| WHSV Benzene | 30 | 30 | 30 | 30 | 30 | 30 |
| WHSV Propylene | 2.4 | 2.4 | 2.4 | 2.4 | 2.4 | 2.4 |
| Mole Ratio Benzene/Propylene | 6.6 | 6.6 | 6.6 | 6.6 | 6.6 | 6.6 |
| CONVERSION, Wt % | | | | | | |
| Benzene | 14.0 | 14.3 | 14.1 | 13.7 | 13.1 | 14.0 |
| Propylene | 97.9 | 95.4 | 96.8 | 97.1 | 95.7 | 96.8 |
| SELECTIVITY TO PRODUCTS, Wt % | | | | | | |
| Isopropylbenzene | 88.5 | 90.3 | 94.0 | 94.8 | 96.3 | 96.7 |
| Diisopropylbenzene | 11.1 | 9.0 | 5.8 | 4.9 | 3.5 | 3.1 |
| n-Propylbenzene | 0 | 0 | 0 | 0 | 0 | 0 |
| Other | 0.4 | 0.7 | 0.2 | 0.2 | 0.2 | 0.2 |
| Total | 100.0 | 100.0 | 100.0 | 100.0 | 100.0 | 100.0 |

High benzene conversions of approximately 14% were observed (theoretical maximum = 15%). Selectivity to isopropylbenzene was 90+% and to isopropylbenzene plus diisopropylbenzene (the diisopropylbenzene may be recycled if desired) was a remarkable 99+%. At higher pressures a heterogeneous liquid/solid phase reaction occurred, with excellent overall catalyst performance.

EXAMPLE 3

In a manner similar to that of Example 2, HZSM-12 catalyst performance was tested in the 200–500 psig range. The reaction is summarized in TABLE III. As before, temperature was maintained at 200° C., but this time the mole ratio and WHSV (benzene/propylene) were 6.8/1 and 15.4/1.2, respectively.

TABLE III

| CONDITIONS OF REACTION | | | | |
|---|---|---|---|---|
| Temp. °C. | 200 | 200 | 200 | 200 |
| Press. psig | 200 | 300 | 400 | 500 |
| WHSV Benzene | 15.4 | 15.4 | 15.4 | 15.4 |
| WHSV Propylene | 1.2 | 1.2 | 1.2 | 1.2 |
| Mole Ratio Benzene/Propylene | 6.8 | 6.8 | 6.8 | 6.8 |
| CONVERSION, Wt % | | | | |
| Benzene | 10.8 | 11.8 | 9.3 | 13.3 |
| Propylene | 98.3 | 98.1 | 97.7 | 97.9 |
| SELECTIVITY TO PRODUCTS, Wt % | | | | |
| Isopropylbenzene | 95.7 | 97.0 | 97.8 | 96.4 |
| Diisopropylbenzene | 4.1 | 2.7 | 1.9 | 3.3 |
| n-Propylbenzene | 0 | 0 | 0 | .1 |
| Other | 0.2 | 0.3 | 0.3 | 0.3 |
| Total | 100.0 | 100.0 | 100.0 | 100.0 |

Excellent results were observed in every case, demonstrating the broad range of pressures over which the process is applicable.

EXAMPLE 4

Utilizing the HZSM-12 catalyst described above, the effect of temperature on the reaction was studied. At a pressure of 300 psig a 6.7/1 mole ratio of benzene to propylene was passed over the catalyst at temperature of 100° C. to 300° C. The feed WHSV was 15.2 for benzene and 1.2 for propylene at 100° C. through 200° C., after which it was adjusted to 28.8 for benzene and 2.4 for propylene. The reaction conditions and products are summarized in TABLE IV.

TABLE IV

| CONDITIONS OF REACTION | | | | | | | | | | |
|---|---|---|---|---|---|---|---|---|---|---|
| Temp. °C. | 100 | 125 | 150 | 175 | 200 | 200 | 225 | 250 | 275 | 300 |
| Press. psig | 300 | 300 | 300 | 300 | 200 | 300 | 300 | 300 | 300 | 300 |
| WHSV Benzene | 15.2 | 15.2 | 15.2 | 15.2 | 15.2 | 28.8 | 28.8 | 28.8 | 28.8 | 28.8 |
| WHSV Propylene | 1.2 | 1.2 | 1.2 | 1.2 | 1.2 | 2.4 | 2.4 | 2.4 | 2.4 | 2.4 |
| Mole Ratio Benzene/Propylene | 6.7 | 6.7 | 6.7 | 6.7 | 6.7 | 6.7 | 6.7 | 6.7 | 6.7 | 6.7 |
| CONVERSION, Wt % | | | | | | | | | | |
| Benzene | 0.9 | 7.1 | 12.0 | 10.4 | 11.8 | 11.3 | 11.3 | 12.2 | 12.3 | 12.1 |
| Propylene | 14.9 | 59.0 | 97.9 | 98.4 | 98.1 | 98.1 | 98.4 | 98.1 | 98.0 | 97.8 |
| SELECTIVITY TO PRODUCTS, Wt % | | | | | | | | | | |
| Isopropylbenzene | 86.04 | 92.33 | 97.06 | 97.64 | 96.99 | 95.74 | 94.92 | 93.20 | 91.46 | 85.89 |
| Diisopropylbenzene | — | 2.92 | 2.67 | 2.06 | 2.70 | 3.96 | 4.54 | 5.56 | 4.96 | 3.75 |
| n-Propylbenzenee | 0 | 0 | 0 | 0 | 0 | 0 | .17 | .89 | 3.22 | 9.99 |
| Other | 14.0 | 4.8 | 0.3 | 0.3 | 0.3 | 0.3 | 0.33 | .31 | .38 | .41 |
| Total | 100.0 | 100.0 | 100.0 | 100.0 | 100.0 | 100.0 | 100.0 | 100.0 | 100.0 | 100.0 |

At lower reaction temperatures of 100°–125° C. the selectivity to isopropylbenzene was good but the rate of conversion was relatively low. Both rate of conversion and selectivity increased dramatically at 150° C. and excellent overall performance was observed at from 150° C. to 225° C. At higher temperatures the concentration of n-propylbenzene began to increase and constituted approximately 10% of the reaction product at 300° C.

EXAMPLE 5

In a manner similar to that of the foregoing examples, the effect of rate of feed of the reactants across the HZSM-12 catalyst was studied. Holding the temperature at a constant 200° C. and the pressure at 300 psig, a 6.68/1 mole ratio of benzene to propylene was fed across the catalyst at total feed weight hourly space velocities of 16.3 to 62.5. The results are summarized in TABLE V.

TABLE V

| CONDITIONS OF REACTION | | | |
|---|---|---|---|
| Temp. °C. | 200 | 200 | 200 |
| Press. psig | 300 | 300 | 300 |
| WHSV Benzene | 15.1 | 29.3 | 57.6 |
| WHSV Propylene | 1.2 | 2.4 | 4.9 |
| Mole Ratio Benzene/Propylene | 6.68 | 6.68 | 6.68 |
| CONVERSION, Wt % | | | |
| Benzene | 11.8 | 13.0 | 12.3 |
| Propylene | 98.1 | 99.9 | 96.6 |
| SELECTIVITY TO PRODUCTS, Wt % | | | |
| Isopropylbenzene | 97.0 | 95.0 | 96.4 |
| Diisopropylbenzene | 2.7 | 4.1 | 3.2 |
| n-Propylbenzene | 0 | 0 | 0 |
| Other | 0.3 | 0.9 | 0.4 |
| Total | 100.0 | 100.0 | 100.0 |

The exceptionally high reactivity of the HZSM-12 catalyst is clearly demonstrated by the very high level of propylene conversion and selectivity to the desired isopropylbenzene alkylation product which was obtained over the entire range of feed rates tested.

EXAMPLE 6

To be useful for a practical alkylation process, a desirable catalyst must have sustained activity. Removal of coke deposits which form on the catalyst with use and inhibit its activity is time consuming and may contribute significantly to high operating costs if frequent regeneration is required. To test the aging characteristics of the HZSM-12 catalyst found useful in the present invention, a continuous run lasting almost nine days was conducted. A temperature of 200° C., pressure of 100 psig, WHSV of the benzene/propylene feed of 30.3–30.9/2.4–2.5 and mole ratio 6.7–6.8/1, respectively, was maintained throughout the run. Under these conditions, the benzene and propylene starting materials were in the vapor phase. The results are summarized in TABLE VI.

TABLE VI

| | Catalyst: HZSM-12 Zeolite | | | | |
|---|---|---|---|---|---|
| Stream Time | Conversion Wt % | | Selectivity to Products Wt % | | |
| Hrs. | $C_6H_6$[1] | $C_3H_6$[2] | IPB[3] | DIPB[4] | Other |
| 1 | 13.2 | 98.2 | 88.2 | 11.2 | 0.6 |
| 10 | 13.4 | 97.1 | 88.4 | 10.9 | 0.7 |
| 23 | 13.6 | 98.3 | 88.8 | 10.6 | 0.6 |
| 46 | 13.4 | 97.5 | 89.4 | 9.9 | 0.7 |
| 57 | 13.5 | 97.1 | 89.2 | 10.0 | 0.8 |
| 70 | 13.6 | 96.9 | 89.3 | 10.0 | 0.7 |
| 94 | 13.1 | 94.1 | 89.5 | 9.6 | 0.9 |
| 116 | 13.2 | 93.3 | 89.3 | 9.9 | 0.8 |
| 140 | 12.8 | 91.6 | 89.9 | 9.3 | 0.8 |
| 164 | 12.9 | 87.8 | 89.8 | 9.6 | 0.6 |
| 177 | 13.0 | 89.0 | 89.8 | 9.8 | 0.4 |
| 211 | 13.8 | 92.2 | 90.1 | 9.7 | 0.2 |

[1]$C_6H_6$ — Benzene.
[2]$C_3H_6$ — Propylene.
[3]IPB — Isopropylbenzene.
[4]DIPB — Diisopropylbenzene.

As will be seen the run was continued for a period of almost nine days (211 hours) with only a slight decrease in the level of conversion of the starting materials. High selectivity to isopropylbenzene and to diisopropylbenzene, the latter of which may be recycled, was observed throughout the run.

EXAMPLE 7

As a comparison with the prior art process of making isopropylbenzene via catalytic alkylation of benzene utilizing a zeolitic catalyst (see: U.S. Pat. No. 3,251,897 and Harper et al. Petrochemical Preprints, supra), a sample of rare earth exchange zeolite Y (REY) was tested under conditions similar to those of Example 6. The pressure and temperature were identical (200° C. and 100 psig) and the feed WHSV was similar—benzene/propylene 32.3/2.4, mole ratio 7.2/1. The results are shown in TABLE VII.

TABLE VII

| | CATALYST REY ZEOLITE | | | | |
|---|---|---|---|---|---|
| Stream Time | Conversion Wt. % | | Selectivity to Products Weight % | | |
| Hrs. | $C_6H_6$[1] | $C_3H_6$[2] | IPB[3] | DIPB[4] | Other |
| 2 | 10.9 | 95.6 | 77.5 | 21.1 | 1.4 |
| 3 | 9.6 | 93.9 | 69.7 | 29.3 | 1.0 |
| 4 | 8.0 | 85.4 | 65.3 | 33.3 | 1.4 |
| 5 | 6.2 | 65.3 | 62.6 | 34.0 | 3.4 |

TABLE VII-continued

| | CATALYST REY ZEOLITE | | | | |
|---|---|---|---|---|---|
| Stream Time | Conversion Wt. % | | Selectivity to Products Weight % | | |
| Hrs. | $C_6H_6$[1] | $C_3H_6$[2] | IPB[3] | DIPB[4] | Other |
| 13 | 1.1 | 1.3 | 58.4 | 26.2 | 15.4 |
| 23 | 0.3 | 0 | 69.5 | 0 | 30.5 |

[1]$C_6H_6$ — Benzene
[2]$C_3H_6$ — Propylene
[3]IPB — Isopropylbenzene
[4]DIPB — Diisopropylbenzene Catalyst aging, as exemplified by the dramatic decreases in conversion of starting materials and selectivity to isopropylbenzene with time, is seen to be very rapid, particularly in comparison to the HZSM-12 catalyst of Example 6.

EXAMPLE 8

To demonstrate the desirable aging characteristics and overall performance of the HZSM-12 catalyst when the herein disclosed process is carried out in the liquid phase, an extended run similar to that of Example 6 (vapor phase reaction) was conducted. The test proceeded over a continuous period of eleven days (263 hours) at 200° C. and 500 psig. The feed WHSV for benzene and propylene was approximately 14.2 and 1.6, respectively. Under these conditions, the major organic reactants and products were in the liquid phase while in contact with the catalyst—a heterogeneous liquid/solid state reaction. The results are given in TABLE VIII.

TABLE VIII

| | CATALYST HZSM-12 | | | | |
|---|---|---|---|---|---|
| Stream Time | Conversion Weight % | | Selectivity to Products Wt. % | | |
| Hours | $C_6H_6$[1] | $C_3H_6$[2] | IPB[3] | DIPB[4] | Other |
| 1 | 18.4 | 98.7 | 92.4 | 6.8 | 0.8 |
| 12 | 17.6 | 99.9 | 92.2 | 6.5 | 1.3 |
| 26 | 17.5 | 99.8 | 92.1 | 6.3 | 1.6 |
| 50 | 17.9 | 99.7 | 92.1 | 6.2 | 1.7 |
| 98 | 20.1 | 98.2 | 91.4 | 6.7 | 1.9 |
| 155 | 18.1 | 96.3 | 93.0 | 5.8 | 1.2 |
| 195 | 18.8 | 94.1 | 93.0 | 5.9 | 1.1 |
| 230 | 16.2 | 88.9 | 92.7 | 5.8 | 1.5 |
| 263 | 17.2 | 93.7 | 93.8 | 5.2 | 1.0 |

[1]$C_6H_6$ — Benzene
[2]$C_3H_6$ — Propylene
[3]IPB — Isopropylbenzene
[4]DIPB — Diisopropylbenzene After eleven days of continuous operation under the same conditions of temperature, pressure and feed rate, only a very small decrease in benzene and propylene conversion was observed.

EXAMPLE 9

In a manner similar to that of Example 8, and under the same conditions of reaction, a sample of REY zeolite catalyst was tested for heterogeneous liquid/solid reaction over a four day period of continuous operation. The results are shown in TABLE IX.

TABLE IX

| | CATALYST REY ZEOLITE | | | | |
|---|---|---|---|---|---|
| Stream Time | Conversion Weight % | | Selectivity to Products Wt. % | | |
| Hours | $C_6H_6$[1] | $C_3H_6$[2] | IPB[3] | DIPB[4] | Other |
| 2 | 14.0 | 97.4 | 79.7 | 19.3 | 1.0 |
| 3 | 15.6 | 96.7 | 77.9 | 21.0 | 1.1 |
| 13 | 16.5 | 99.8 | 73.1 | 24.7 | 2.2 |
| 25 | 16.7 | 99.2 | 69.8 | 27.0 | 3.2 |

TABLE IX-continued

| | CATALYST REY ZEOLITE | | | | |
|---|---|---|---|---|---|
| Stream Time | Conversion Weight % | | Selectivity to Products Wt. % | | |
| Hours | $C_6H_6$[1] | $C_3H_6$[2] | IPB[3] | DIPB[4] | Other |
| 45 | 17.5 | 97.1 | 67.2 | 28.5 | 4.3 |
| 48 | 16.8 | 95.8 | 68.3 | 27.5 | 4.2 |
| 60 | 9.9 | 57.7 | 72.7 | 23.5 | 3.8 |
| 70 | 3.8 | 20.0 | 87.9 | 11.2 | 0.9 |
| 84 | 3.9 | 14.0 | 95.8 | 4.2 | — |
| 94 | 1.4 | 11.2 | 100 | 0 | — |

[1]$C_6H_6$ — Benzene
[2]$C_3H_6$ — Propylene
[3]IPB — Isopropylbenzene
[4]DIPB — Diisopropylbenzene While it is evident that the REY afforded a high rate of conversion during the first two days of operation, it can be seen that very rapid catalyst aging occurred in the third and fourth days on stream. Further, the production of diisopropylbenzene is shown to be roughly 2.5 times greater than the corresponding run with the HZSM-12 catalyst (Example 8).

EXAMPLE 10

Mixtures of propane and propylene are availabe in refineries and olefin manufacturing facilities at substantially lower cost than that of purified propylene. To simulate such a feed stream, a mixture of approximately equimolar amounts of propane and propylene was supplied to the alkylation reactor containing the HZSM-12 catalyst along with the benzene feed. The reaction was carried out at a constant 200° C. and 500 psig and the molar ratio of benzene to propylene was varied from 12.5/1 through 1.81/1. The results are summarized in TABLE X.

TABLE X

| CONDITIONS OF REACTION | | | | | | | |
|---|---|---|---|---|---|---|---|
| Temp. °C. | 200 | 200 | 200 | 200 | 200 | 200 | 200 |
| Press. psig | 500 | 500 | 500 | 500 | 500 | 500 | 500 |
| WHSV Benzene | 14.5 | 14.5 | 14.5 | 14.5 | 14.5 | 14.5 | 14.5 |
| WHSV Propylene | .62 | 1.25 | 1.87 | 2.39 | 3.12 | 3.74 | 4.36 |
| WHSV Propane | .58 | 1.24 | 1.75 | 2.33 | 2.91 | 3.49 | 4.07 |
| Mole Ratio: | | | | | | | |
| $C_6H_6$ | 12.5 | 6.24 | 4.16 | 3.12 | 2.50 | 2.11 | 1.81 |
| $C_3H_6$ | 1 | 1 | 1 | 1 | 1 | 1 | 1 |
| $C_3H_8$ | .89 | .89 | .89 | .89 | .89 | .89 | .89 |
| Conversion, Wt. % | | | | | | | |
| Benzene | 7.1 | 14.5 | 22.4 | 28.4 | 34.3 | 40.0 | 41.3 |
| Propylene | 99.8 | 99.9 | 99.7 | 99.9 | 99.9 | 98.3 | 98.1 |
| Selectivity to Products, Wt. % | | | | | | | |
| Isopropylbenzene | 99.50 | 95.72 | 91.79 | 88.31 | 84.90 | 81.67 | 79.97 |
| Diisopropylbenzene | 0 | 4.14 | 7.23 | 10.48 | 13.64 | 16.49 | 17.01 |
| n-Propylbenzene | 0 | 0 | .04 | .09 | .09 | .09 | .07 |
| Other | 0.5 | 0.1 | 1.0 | 1.2 | 1.5 | 1.8 | 3.0 |
| Total | 100.0 | 100.0 | 100.0 | 100.0 | 100.0 | 100.0 | 100.0 |

The propane passed through the catalyst bed without reacting and was recovered with the reaction products. Virtually all of the propylene feed was reacted, illustrating the high activity of the HZSM-12 catalyst. As expected, the highest selectivity to the isopropylbenzene alkylation product occurred at the 12.5/1 molar feed ratio of benzene to propylene. As the feed ratio was reduced, the yield of the diisopropylbenzene increased along with the other (higher boiling) products. The example also clearly demonstrates the high activity of the catalyst at relatively low temperature and in a heterogeneous liquid/solid system.

EXAMPLE 11

In a manner similar to that described in Example 10, an approximately equimolar mixture of propane and propylene was used to alkylate benzene at various temperatures in the presence of HZSM-12 catalyst. The pressure was maintained at 500 psig and the molar ratio of benzene to propylene was 6.3/1 with a feed WHSV of 14.6 for benzene, 1.25 for propylene and 1.16 for propane. TABLE XI is a summary of the results.

TABLE XI

| CONDITIONS OF REACTION | | | | | | |
|---|---|---|---|---|---|---|
| Temp. °C. | 150 | 175 | 200 | 225 | 250 | 300 |
| Press. psig | 500 | 500 | 500 | 500 | 500 | 500 |
| WHSV Benzene | 14.6 | 14.6 | 14.6 | 14.6 | 14.6 | 14.6 |
| WHSV Propylene | 1.25 | 1.25 | 1.25 | 1.25 | 1.25 | 1.25 |
| WHSV Propane | 1.16 | 1.16 | 1.16 | 1.16 | 1.16 | 1.16 |
| Mole Ratio: | | | | | | |
| $C_6H_6$ | 6.3 | 6.3 | 6.3 | 6.3 | 6.3 | 6.3 |
| $C_3H_6$ | 1 | 1 | 1 | 1 | 1 | 1 |
| $C_3H_8$ | .89 | .89 | .89 | .89 | .89 | .89 |
| Conversion Wt. % | | | | | | |
| Benzene | 11.5 | 12.9 | 14.5 | 15.1 | 15.2 | 14.9 |
| Propylene | 99.8 | 99.5 | 99.9 | 99.9 | 99.9 | 99.9 |
| Selectivity to Products, Wt. % | | | | | | |
| Isopropylbenzene | 96.91 | 96.23 | 95.72 | 93.77 | 93.11 | 80.75 |
| Diisopropylbenzene | 2.80 | 3.61 | 4.14 | 5.73 | 5.95 | 4.17 |
| n-Propylbenzene | 0 | 0 | 0 | .18 | .65 | 13.77 |
| Other | 0.3 | 0.2 | 0.1 | 0.3 | 0.2 | 1.3 |
| Total | 100.0 | 100.0 | 100.0 | 100.0 | 100.0 | 100.0 |

In every case, virtually all of the propylene in the feed mixture was converted to alkylation products. Significant amounts of n-propylbenzene appeared at 300° C., representing the upper practical temperature limit of operation under this combination of operating conditions. The results of this and the foregoing Example 10 indicate that the relatively low cost refinery and olefin plant propane/propylene streams can be desirably utilized in this process for the direct product of isopropylbenzene.

EXAMPLE 12

In many of the foregoing examples, where ZSM-12 zeolite was used as the alkylation catalyst, the selectivity to isopropylbenzene was in the 90-97% range. Diisopropylbenzene was the principal component in the remaining higher boiling by-products. In a commercial process it would be avantageous to convert these materials to the desired product. This was demonstrated by mixing diisopropylbenzene and higher isopropylated aromatic compounds, such as triisopropylbenzene with benzene (fresh feed or recycle) and passing the mixture over the HZSM-12 zeolite catalyst at 200° C. and a WHSV of 3-4. More detailed results are summarized in Table XII.

TABLE XII

| | Catalyst: HZSM-12 | | | | | |
|---|---|---|---|---|---|---|
| Temp. °C. | 200 | 250 | 200 | 250 | 200 | 250 |
| Pressure PSIG | 0 | 0 | 0 | 0 | 0 | 0 |
| WHSV Benzene | 3.20 | 3.20 | 3.20 | 3.20 | 3.20 | 3.20 |
| WHSV DIPB | .24 | .24 | — | — | — | — |
| WHSV NPRBZ | — | — | .24 | .24 | — | — |
| WHSV TIPB | — | — | — | — | .24 | .24 |
| Conversion, Wt. % | | | | | | |
| Benzene | 0.9 | 2.2 | 0 | 0.1 | 1.5 | 1.8 |
| DIPB | 79.4 | 96.9 | — | — | — | — |
| NPRBZ | — | — | 0 | 1.8 | — | — |
| TIPB | — | — | — | — | 50.0 | 95.3 |
| Selectivity to | | | | | | |
| Products, Wt. % | | | | | | |
| Isopropylbenzene | 100.0 | 92.0 | — | 100.0 | 85.0 | 93.2 |
| NPRBZ | — | 7.0 | — | — | — | 3.3 |
| DIPB | — | — | — | — | 15.0 | 3.5 |
| Other Aromatics | — | 1.0 | — | — | — | — |
| TOTAL | 100.0 | 100.0 | — | 100.0 | 100.0 | 100.0 |

Note:
DIPB = Diisopropylbenzene
NPRBZ = n-Propylbenzene
TIPB = Triisopropylbenzene At 200° C., 79.4% of the diisopropylbenzene (mixture of isomers) was converted to isopropylbenzene exclusively. At 250° C. The conversion was increased to 96.9%, however, the especially undesirable n-propylbenzene and some other aromatic compounds were produced.

In a similar manner, at 200° C., when 1,3,5-triisopropylbenzene in benzene was used as the feed, 50% conversion was observed with a selectivity of 85% to the desired isopropylbenzene and 15% to diisopropylbenzenes which could be recycled again.

n-Propylbenzene was relatively unreactive, but the small amount converted at 250° C. rearranged to form isopropylbenzene.

Transalkylation of the major side reaction components readily occurs with the benzene feed to produce the desired isopropylbenzene.

It is to be understood that the foregoing description is intended to be merely illustrative of certain preferred embodiments of this invention, of which many variations may be made by those skilled in the art within the scope of the following claims without departing from the spirit thereof.

What is claimed is:

1. A process for the propylation of benzene with selective production of isopropylbenzene, said process comprising contacting mixtures of benzene and propylene with a crystalline zeolite catalyst at a temperature of between about 100° C. and the critical temperature, and a pressure of between about $10^5$ N/m$^2$ and $6 \times 10^6$ N/m$^2$, said zeolite being characterized by a silica/alumina mole ratio of at least about 12 and a constraint index within the approximate range of 1 to 12, said zeolite being 2 sm-12.

2. The process of claim 1 wherein the molar ratio of benzene to propylene is within the approximate range of 12 to 1.

3. The process of claim 1 wherein contact between said benzene/propylene mixture and said zeolite is at a temperature of between about 150° C. and about 250° C.

4. The process of claim 1 wherein said benzene/propylene mixture is contacted with said zeolite catalyst as a continuous stream at a weight hourly space velocity of from about 0.05 to about 100.

5. The process of claim 4 wherein said weight hourly space velocity is between about 5 and about 40.

6. The process of claim 1 wherein said benzene/propylene mixture is in the vapor phase.

7. The process of claim 1 wherein said benzene/propylene mixture is in the liquid phase.

8. The process of claim 1 wherein said propylene feed contains a substantial amount of propane in admixture therewith.

9. The process of claim 1 wherein said zeolite is combined with a binder therefor.

10. The process of claim 1 wherein dialkylbenzene, trialkylbenzene and n-propylbenzene are byproducts of said selective propylation reaction, said byproducts being recycled over said catalyst to effect transalkylation to isopropylbenzene.

* * * * *

UNITED STATES PATENT OFFICE
CERTIFICATE OF CORRECTION

Patent No. 4,393,262                 Dated July 12, 1983

Inventor(s) Warren W. Kaeding

It is certified that error appears in the above-identified patent and that said Letters Patent are hereby corrected as shown below:

Column 1, line 16, "unit" should read --units--;

Column 4, line 52, before "treated" insert --so--;

Column 14, line 43, "2sm-12" should read --ZSM 12--;

Column 14, line 52, "0.05" should read --0.5--.

Signed and Sealed this

Thirteenth Day of March 1984

[SEAL]

*Attest:*

*Attesting Officer*

GERALD J. MOSSINGHOFF

*Commissioner of Patents and Trademarks*